United States Patent
Webb et al.

(10) Patent No.: US 9,724,439 B2
(45) Date of Patent: *Aug. 8, 2017

(54) AUTOCLAVE STERILIZATION CABINET

(71) Applicant: PMBS, LLC, Stockton, NJ (US)

(72) Inventors: Alexis Douglas Webb, Clearwater, FL (US); Jesus Manuel Pazos, Tampa, FL (US); Randel Scott Kristich, Seminole, FL (US)

(73) Assignee: PMBS, LLC, Stockton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/233,384

(22) Filed: Aug. 10, 2016

(65) Prior Publication Data
US 2016/0346415 A1    Dec. 1, 2016

Related U.S. Application Data

(63) Continuation of application No. 14/861,620, filed on Sep. 22, 2015, now Pat. No. 9,439,992, which is a
(Continued)

(51) Int. Cl.
*A47B 91/00* (2006.01)
*A61L 2/07* (2006.01)
(Continued)

(52) U.S. Cl.
CPC ............... *A61L 2/07* (2013.01); *A47B 81/00* (2013.01); *A61L 2/00* (2013.01); *A61L 2/26* (2013.01);
(Continued)

(58) Field of Classification Search
CPC .......... Y10T 16/541; E05D 3/12; E05D 3/122
(Continued)

(56) References Cited

U.S. PATENT DOCUMENTS 4,783,321 A * 11/1988 Spence ................ A61L 2/26
                                                    206/439
4,915,918 A *  4/1990 Nichols ............... A61L 2/26
                                                    206/363
(Continued)

OTHER PUBLICATIONS

Wagner Sterilsystem, The SteriSet System, pp. 6-7, May 6, 2005, https://web.archive.org/web/20050506101217/http://www.wagner-steriset.de/html/m01E23.htm.†
(Continued)

*Primary Examiner* — Matthew Ing (57) ABSTRACT

A sterilization cabinet for use in an autoclave. The sterilization cabinet includes one or more filtered vents permitting sterilization agent to enter and exit the interior space of the cabinet during a sterilization cycle. Each vent is occluded by a cover plate. The cover plate contains a latch configured to accept a rod extending from the center of the vent and engage a notch disposed thereon. The floor of the cabinet is shaped to direct the liquid contained within the cabinet to flow into the drain port disposed within the floor. The drain assembly is used to expel the liquid from the cabinet while preventing microbes and contaminants from entering the cabinet. The hinges connecting the door to the cabinet can be used to adjust an angle of inclination, a horizontal position, and a vertical position of the door.

20 Claims, 7 Drawing Sheets

Related U.S. Application Data continuation-in-part of application No. 14/644,094, filed on Mar. 10, 2015.

(60) Provisional application No. 61/950,502, filed on Mar. 10, 2014, provisional application No. 62/053,338, filed on Sep. 22, 2014.

(51) Int. Cl.

| | |
|---|---|
| *A61L 2/26* | (2006.01) |
| *A47B 81/00* | (2006.01) |
| *F16J 15/06* | (2006.01) |
| *B01D 46/00* | (2006.01) |
| *A61L 2/00* | (2006.01) |
| *B60B 33/00* | (2006.01) |
| *A61L 9/00* | (2006.01) |
| *B01D 35/02* | (2006.01) |

(52) U.S. Cl.
CPC ............... *A61L 9/00* (2013.01); *B01D 35/02* (2013.01); *B01D 46/0005* (2013.01); *B60B 33/00* (2013.01); *F16J 15/06* (2013.01); *A61L 2202/24* (2013.01); *B01D 2273/20* (2013.01); *B01D 2279/35* (2013.01); *Y10T 29/49828* (2015.01)

(58) Field of Classification Search
USPC .................................. 312/229, 236, 200, 201
See application file for complete search history.

(56) References Cited

U.S. PATENT DOCUMENTS

| | | | | |
|---|---|---|---|---|
| 5,324,489 | A | * | 6/1994 | Nichols ..................... A61L 2/26 206/363 |
| 5,968,459 | A | * | 10/1999 | Nalepa ...................... A61L 2/07 206/439 |
| 7,001,441 | B2 | * | 2/2006 | Bauer ...................... A61L 2/022 206/438 |
| 8,454,901 | B1 | * | 6/2013 | Snyder, III ................ A61L 2/07 422/26 |
| 2013/0322004 | A1 | * | 12/2013 | Park ........................ F16C 11/10 361/679.27 |
| 2015/0107627 | A1 | * | 4/2015 | Snyder ................... A61B 90/70 134/22.1 |

OTHER PUBLICATIONS

Wagner Sterilsysteme, "Or Filter After All?", pp. 4-5, Aug. 25, 2005, https://web.archive.org/web/20110112052317/http://www.wagner-steriset.de/images/PDFs/Container/SteriSet_Rundfilter_2003.pdf.†

Wagner Sterilsysteme, The SteriSet System, pp. 1-3, Aug. 25, 2005, https://web.archive.org/web/20050825213235/http://www.wagner-steriset.de/html/m01E21.htm.†

* cited by examiner
† cited by third party

AUTOCLAVE STERILIZATION CABINET

CROSS REFERENCE TO RELATED APPLICATIONS

This application is a continuation of and claims priority to U.S. patent application Ser. No. 14/861,620, entitled "Autoclave Sterilization Cabinet" filed on Sep. 22, 2015, which application is a continuation-in-part of and claims priority to U.S. patent application Ser. No. 14/644,094, entitled "Mobile Sterilization Apparatus And Method For Using The Same" filed on Mar. 10, 2015, which claims priority to U.S. provisional application Ser. No. 61/950,502 filed on Mar. 10, 2014 and U.S. provisional application Ser. No. 62/053,338 filed on Sep. 22, 2014, the contents of which are hereby incorporated by reference.

BACKGROUND OF THE INVENTION

1. Field of the Invention

This invention relates to an autoclave sterilization cabinet. More specifically, it relates to a sterilization cabinet configured to house medical instruments during a sterilization cycle and maintain them in a sterile environment after sterilization.

2. Brief Description of the Related Art

It has become axiomatic in modern medicine that the medical instruments used during a medical procedure must be sterile. Most medical facilities use autoclaves to sterilize medical instruments. Sterilization in autoclaves is achieved by subjecting medical instruments to sterilizing agent at high temperatures and pressures for a predetermined period of time. Traditionally, medical instruments are placed onto trays, which are individually wrapped in a protective wrap. The trays are then loaded onto a cart and placed into an autoclave. After the sterilization cycle, the protective wrap maintains sterility of the medical instruments contained therein. The instruments remain within the protective wrap until they are needed for a procedure.

In the recent years, mobile sterilization cabinets such as the ones disclosed in U.S. Pat. No. 8,454,901 and U.S. Pub. App. No. 2015/0209455 have emerged. Sterilization cabinets do not require that each tray is wrapped into a protective wrap. Instead, the sterilization cabinet itself ensures sterility of the medical instruments contained therein after a sterilization cycle. Medical instruments are loaded onto trays and are placed into the sterilization cabinet, which is then placed into an autoclave. Sterilization cabinet contains a plurality of filtered vents which permit sterilization agent to flow therethrough during a sterilization cycle, but prevent microbes and contaminants from entering the sterilization cabinet, thereby maintaining sterile conditions after the sterilization cycle has been completed.

The sterilization cabinets currently known in the art, however, suffer from several major flaws. First, the cabinets lack a mechanism for properly expelling liquid condensate that remains within the cabinet after the sterilization cycle. This is problematic because the liquid can lead to mold growth and can serve as a conduit for microbes to enter the cabinet through a wet filter. Second, filter covers and the means of securing filter covers over the vents are inconvenient to operate and may compromise the structural strength of the sterilization cabinet. Third, manufacturing inconsistencies and deformation the sterilization cabinet may undergo during the assembly process may misalign the door with respect to the access port of the cabinet, but the sterilization cabinets known in the art do not account for this and do not provide a mechanism for efficiently adjusting the alignment of the door.

Accordingly, there exists a need for an improved autoclave sterilization cabinet having a mechanism for expelling the liquid condensate, an improved mechanism for securing the cover plates over the vents, and a mechanism for adjusting the alignment of the door.

SUMMARY OF THE INVENTION

The long-standing but heretofore unfulfilled need for an autoclave sterilization cabinet having a mechanism for expelling the condensate from the interior of the sterilization cabinet, an improved vent mechanism, and a door whose alignment can be efficiently adjusted is now met by a new, useful, and nonobvious invention.

In an embodiment, the sterilization cabinet has a roof, a lateral wall, and a floor, which collectively form the body of the sterilization cabinet. The body of the sterilization cabinet has an access port defined by proximal edges of the roof, the lateral wall, and the floor. A door is connected to the body of the sterilization cabinet. When the door is in its closed configuration, the door encloses the interior space of the sterilization cabinet by occluding the access port. The door forms an air-tight, fluid-impermeable seal with the body of the cabinet. The fluid-impermeable seal cannot be penetrated by gases, liquids, microbes, or other contaminants, thereby isolating the interior space of the sterilization cabinet from the environment.

The body of the cabinet contains at least one vent port. A cover plate is positioned over that vent port. The cover plate forms an air-tight, fluid-impermeable seal with the exterior surface of the body of the sterilization cabinet. The fluid-impermeable seal cannot be penetrated by gases, liquids, microbes, or other contaminants, thereby isolating the interior space of the sterilization cabinet from the environment and maintaining sterile conditions within the cabinet. The cover plate contains an aperture that at least partially coincides with the vent port.

A filter is sandwiched between the body of the sterilization cabinet and the cover plate. The filter occludes the area where the vent port and the opening of the cover plate coincide. Accordingly, in order to enter or exit the interior space of the sterilization cabinet, the sterilization agents, such as steam and hot air, must pass through the filter.

The sterilization cabinet further contains a drain port positioned at the lowest point of the cabinet's floor. The floor has a shape configured to channel the liquid into the drain port. A drain assembly is positioned at the drain port. The drain assembly contains a filter sealingly enclosed therein. The drain assembly enables the liquid condensation within the container to exit the container through the filter. The filter prevents contaminants outside the sterilization cabinet from entering the cabinet through the drain port. Consequently, when the door is in its closed configuration, all sterilization agents flow between interior space of the sterilization cabinet and an external environment must pass through the vent filter, the drain filter, or both.

In an embodiment, at least one vent port is disposed within the lateral wall of the sterilization cabinet. A second vent port may be disposed within the same plane as the first vent port. Another pair of vent ports may be positioned on the lateral wall panel opposite the panel on which the first pair of vent ports is located.

In an embodiment, the vent port may be made up of a plurality of apertures within the body of the sterilization cabinet. The apertures may be tear-shaped, circular, oval, elliptical, polygonal, or any other shape. To reduce points of concentrated stress, vent apertures are preferably free of sharp corners.

In an embodiment, the cover plate contains a latch. A rod extends from the body of the sterilization cabinet. The rod has a notch on its free end. The latch has an opening through which the latch accepts the rod. The latch engages the notch which causes the latch to exert a force onto the cover plate. The latch retains the cover plate in a position in which the cover plate occludes the vent port.

In an embodiment, a gasket is disposed on the cover plate. The force applied onto the cover plate by the latch causes the gasket to undergo an elastic deformation thereby creating the fluid-impermeable seal between the cover plate and the body of the sterilization cabinet. The fluid-impermeable seal cannot be penetrated by gases, liquids, microbes, or other contaminants, thereby isolating the interior space of the sterilization cabinet from the environment.

In an embodiment, a wire mesh is disposed on the cover plate and occludes the aperture of the cover plate.

In an embodiment, a reinforcement plate is disposed within the body of the sterilization cabinet. The reinforcement plate has an opening at least partially coinciding with the vent port thereby permitting sterilization agent flow therethrough.

In an embodiment, one or more hinge assemblies connect the door to the body of the sterilization cabinet. The hinge assembly has a hinge base which is affixed to the body of the sterilization cabinet. The hinge base contains a hole configured to accept a hinge shaft. A hinge arm is pivotally connected to the hinge base via hinge shaft. A second hinge arm is affixed to the door. A hinge link is pivotally connected to the first hinge arm and the second hinge arm. The hinge link has two pivot axes which enable the door to rotate with respect to the body of the sterilization cabinet by at least 270 degrees. The angle of inclination, horizontal position, and vertical position of the door can be adjusted by adjusting positions or angles of the hinge base, the hinge shaft, and the first hinge arm. In an embodiment, these adjustment may be made by adjusting set screws within the hinge assemblies.

In an embodiment, the first hinge arm contains a first gear and the second hinge arm contains a second gear. The first and the second gears engage one another, thereby stabilizing the movement of the door while it is being opened or closed.

DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiment, reference is made to the accompanying drawings, which form a part hereof, and within which specific embodiments are shown by way of illustration by which the invention may be practiced. It is to be understood that other embodiments may be utilized and structural changes may be made without departing from the scope of the invention.

Figure 1:
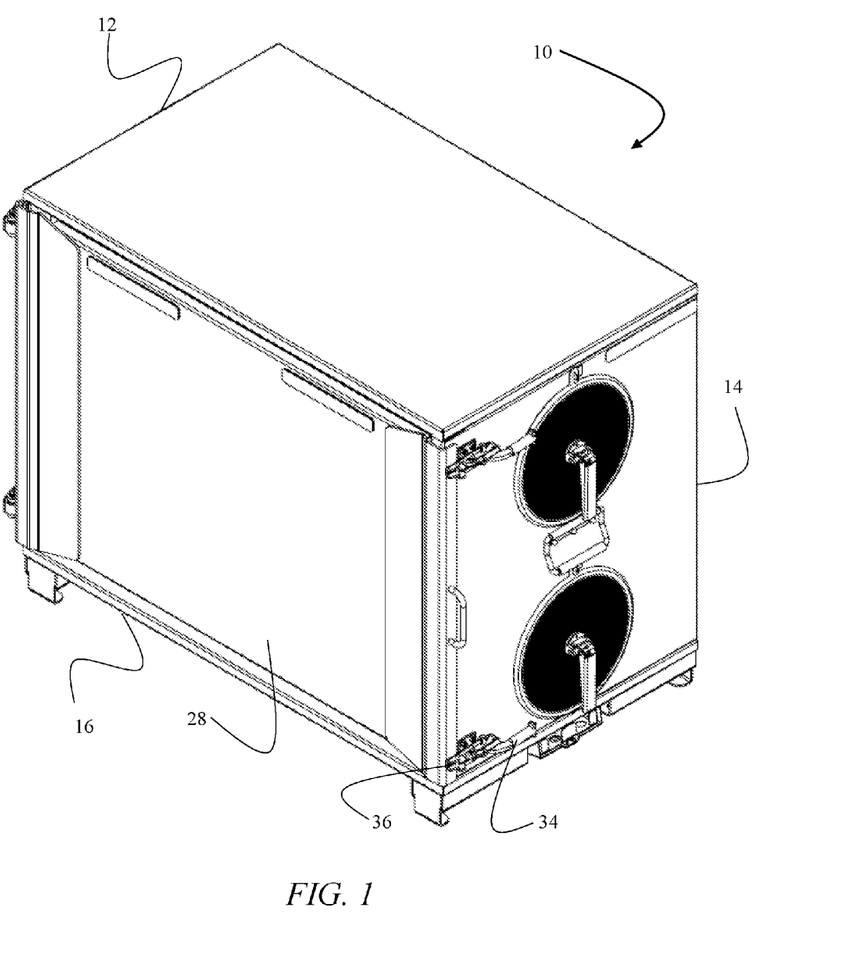
FIG. 1 is a perspective view of the sterilization cabinet according to the invention.

FIG. 1 depicts an autoclave sterilization cabinet 10 according to the invention. Sterilization cabinet 10 comprises a roof 12, a lateral wall 14, and a floor 16. In the embodiment depicted in FIG. 1, lateral wall 14 is made up of three rectilinear sections. In alternative embodiments, lateral wall 14 may be curved, may comprise multiple rectilinear sections, or a combination of rectilinear and curved surfaces. In an embodiment depicted in FIG. 2, lateral wall 14 is manufactured as a single unit. Lateral wall 14 has a top flange 18 and a bottom flange 20 disposed respectively on the top and bottom edges of lateral wall 14. Roof 12 and floor 16 have flanges 22 and 24 disposed on the edges thereof. Flange 22 of roof 12 is configured to be welded, fastened, or otherwise mated with top flange 18 of lateral wall 14, and flange 24 of floor 16 is configured to be welded, fastened, or otherwise mated with bottom flange 20 of lateral wall 14, thereby forming the body of sterilization cabinet 10 as depicted in FIG. 3. Proximal edges of roof 12, lateral wall 14, and floor 16 define an access port 26 of cabinet 10, wherein the interior space partially enclosed by roof 12, lateral wall 14, and floor 16 can be accessed through access port 26.

Figure 4:
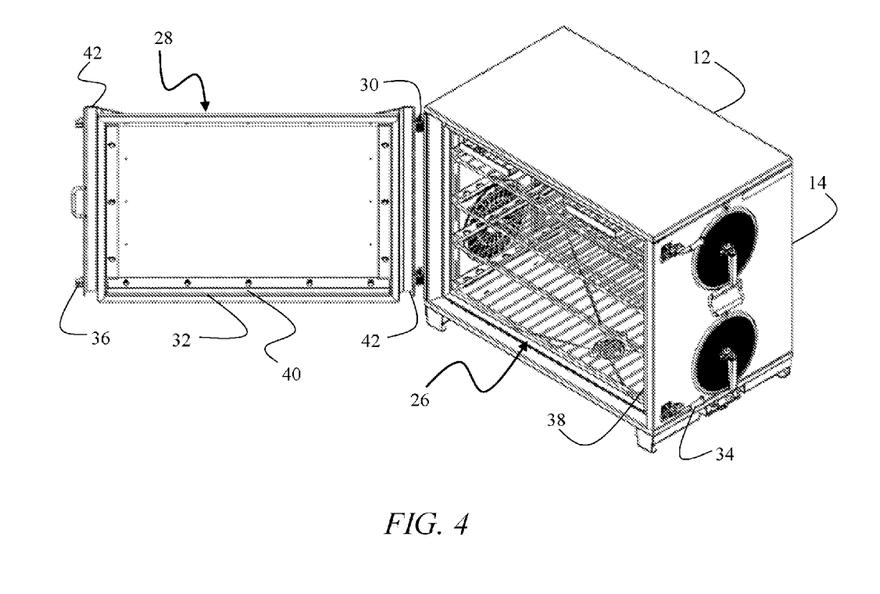
FIG. 4 is a perspective view of the sterilization cabinet depicting the door in an open configuration.

Referring to FIG. 4, door 28 is hingedly attached to lateral wall 14 via hinge assemblies 30. Door 28 is configured to sealingly enclose the inner space of sterilization cabinet 10 when door 20 is in a closed configuration. A gasket 32 may be disposed on the inner periphery of door 28 to create an air-tight, fluid-impermeable seal between door 28 and sterilization cabinet 10 when door 28 is in a closed configuration. The fluid-impermeable seal cannot be penetrated by gases, liquids, microbes, or other contaminants, thereby isolating the interior space of the sterilization cabinet from the environment.

As depicted in FIG. 1, one or more door latches 34 are used to retain door 28 in the closed configuration. Door latches 34 are affixed to lateral side 14, and corresponding hooks 36 are affixed to door 28. In the closed configuration, door latches 34 engage and retain hooks 36, thereby securing door 28 in the closed configuration. In their locked configuration, door latches 34 are configured to compress gasket 32, thereby creating a fluid-impermeable seal between door 28 and access port 26. The fluid-impermeable seal cannot be penetrated by gases, liquids, microbes, or other contaminants, thereby isolating the interior space of the sterilization cabinet from the environment. In alternative embodiments, any other locking mechanisms known in the art for retaining a hingedly attached door in a closed configuration may be used instead of the hooks-latch assemblies.

As depicted in FIG. 4, access port 26 has an outwardly extending lip 38 around its periphery. Door 28 has a complimentary lip 40 on its inner surface. Gasket 32 is disposed around lip 40. In alternative embodiment gasket 32 may be affixed to cabinet 10 around lip 38 of access port 26. Door 28 may further include U-shaped brackets 42 configured to accept proximal edges of lateral wall 14. Hinge assemblies 30 and latch hooks 36 may be disposed on brackets 42.

Figure 5:
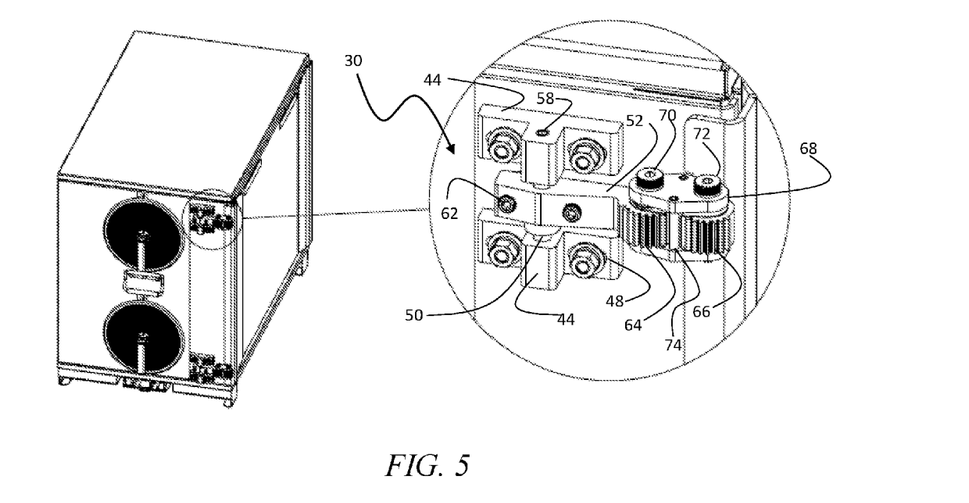
FIG. 5 is an enlarged perspective view of the hinge connecting the door to the body of the sterilization cabinet.
Figure 6:
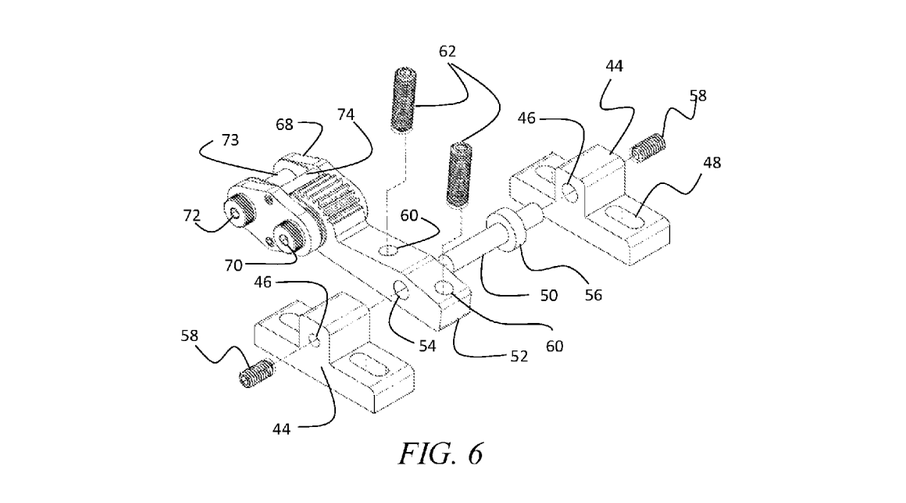
FIG. 6 is an exploded perspective view of the hinge.

Hinge assembly 30 is depicted in FIG. 5 and FIG. 6. Hinge assembly 30 comprises two base brackets 44. Each base bracket 44 has an aperture 46 configured to accept hinge shaft 50. Base brackets 44 further contain two elongated holes 48 for fastening base bracket 44 to lateral wall 14 of sterilization cabinet 10. Elongated holes 48 permit linear adjustment of each base bracket 44 in the direction of the elongation of holes 48. Base brackets 44 can be adjusted independently of one another, and therefore, inclination of hinge shaft 50 with respect to a vertical direction can be precisely adjusted. This configuration is accomplished by positioning base brackets 44 such that the desired inclination of hinge shaft 50 is achieved. The inclination of hinge shaft 50 is critical to ensure that door 28 is adequately aligned with access port 26 when door 28 is in its closed configuration. By adjusting inclination of hinge shaft 50, the angle of inclination of door 28 with respect to access port 26 may be adjusted, thereby bringing door 28 into proper alignment with access port 26.

Hinge assembly 30 further comprises a hinge arm 52. Hinge arm 52 contains a through hole 54 configured to accept hinge shaft 46. Hinge shaft 46 contains a stop 56 having a diameter larger than the diameter of through hole 54, thereby retaining hinge arm 52 at a set position along hinge shaft 46. Aperture 46 of lower base bracket 44 contains a female thread. A base set screw 58 is configured to mate with the female thread within aperture 46. Base set screw 58 is used to adjust the position of stop 56 in the vertical direction. This allows to ensure that hinge arm 52 is set a height at which door 28 vertically aligns with access port 26 when door 28 is in its closed configuration. A second set screw 58 may disposed within the upper base bracket 44 to immobilize hinge shaft 46 against vertical movement.

Hinge arm 52 further contains two threaded holes 60 disposed in the transverse plane of hinge arm 52. Threaded holes 60 are positioned on both sides of through hole 54, which accepts hinge shaft 46. Set screws 62 are configured to mate with threaded holes 60. Distal ends of set screws 62 abut the exterior surface of lateral wall 14, thereby immobilizing hinge arm 52 against rotation about hinge shaft 46. Set screws 62 are used to adjust the angle of hinge arm 52 in a horizontal plane. By adjusting the angle of hinge arm 52, the alignment of door 28 is adjusted to ensure that door 28 horizontally aligns with access port 26 when door 28 is in its closed configuration.

Roof 12, lateral walls 14, and floor 16 of cabinet 10 can undergo some deformation during assembly of cabinet 10. The structure of hinge assemblies 30 disclosed herein allows to adjust the angle of inclination, the horizontal alignment, and the vertical alignment of door 28 with respect to access port 26 by simply adjusting the positions of base brackets 44 and set screws 58 and 62. Accordingly, hinge assemblies 30 enable door 28 to be affixed to sterilization cabinet 10 in a way that ensures proper alignment of door 28 and access port 26 when door 28 is in its closed configuration regardless of manufacturing irregularities or deformation roof 12, lateral wall 14, and floor 16.

Hinge arm 52 contains a first gear 64 disposed thereon. A second gear 66 configured to mate with first gear 64 is disposed on door 28. A hinge link 68 has two pivot axes 70 and 72. First gear 64 and second 66 are both pivotally attached to hinge link 68 at pivot axes 70 and 72. In this configuration, first gear 64 and second gear 66 engage one another, thereby enable door 28 to pivotally rotate by 270°. First and second gears 64 and 66 facilitate smooth motion of door 28. Dampers 73 may be used to allow door 28 to stop at any angle of rotation. Safety rods 74 may be disposed on hinge link 68 to prevent foreign objects from getting caught between first and second gears 64 and 66.

Figure 7:
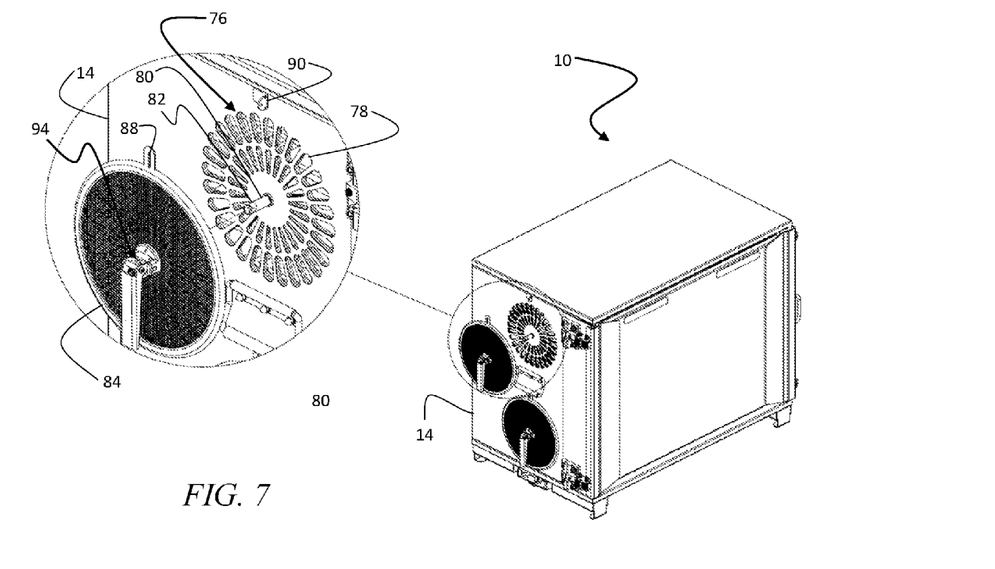
FIG. 7 is an enlarged perspective view of the vent and the cover plate.

Referring to FIG. 7, sterilization cabinet 10 contains a plurality of vent ports 76 disposed on lateral wall 14. Vent ports 76 are configured to permit a fluid (i.e. sterilization agents, such as steam and hot air) to flow in and out of the interior space of sterilization cabinet 10. Each vent 76 is made up of a plurality of apertures 78 disposed within lateral wall 14. FIG. 7 illustrates that apertures 78 are tear-shaped and are disposed radially about a center of the vent, thereby forming a circular configuration. This design maximizes the total area through which sterilization agents can pass, while maintaining structural integrity of lateral wall 14. Since apertures 78 do not have angled corners, the tear-shape design eliminates the points of stress concentration. Structural integrity of later wall 14 is critical for sterilization cabinet 10 because sterilization cabinet must withstand high temperatures and pressures of the autoclave without undergoing plastic deformation or experiencing fatigue. FIG. 7 depicts vent 76 comprising two radial rows of tear-shaped apertures 78. It is to be understood, however, that other shapes of apertures 78 fall within the scope of the invention—for example, apertures 78 may be circular, oval, rectilinear, polygonal, or any other shape. The arrangement of apertures 78 may also depart from the embodiment depicted in the drawings: vent ports 76 may be oval, rectilinear, polygonal, or any other shape. In an alternative embodiment, vent 76 may comprise a single large aperture 78 rather than a plurality of smaller apertures 78.

Figure 8:
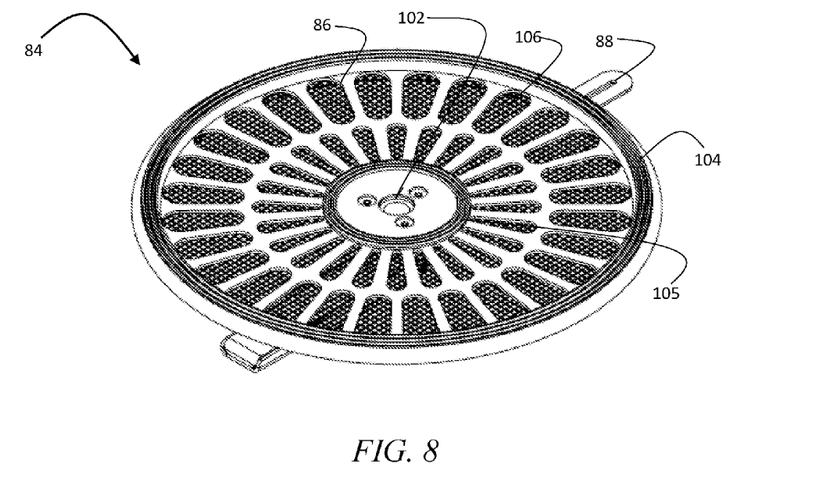
FIG. 8 is a perspective view depicting an interior surface of the cover plate.

A rod 80 extends from lateral wall 14 at the center of vent 76. Rod 80 is substantially perpendicular to lateral wall 14. The proximal end of rod 80 contains a notch 82. FIG. 8 depicts a cover plate 84 that is configured to receive rod 80 through an opening 102 disposed therein.

Figure 9:
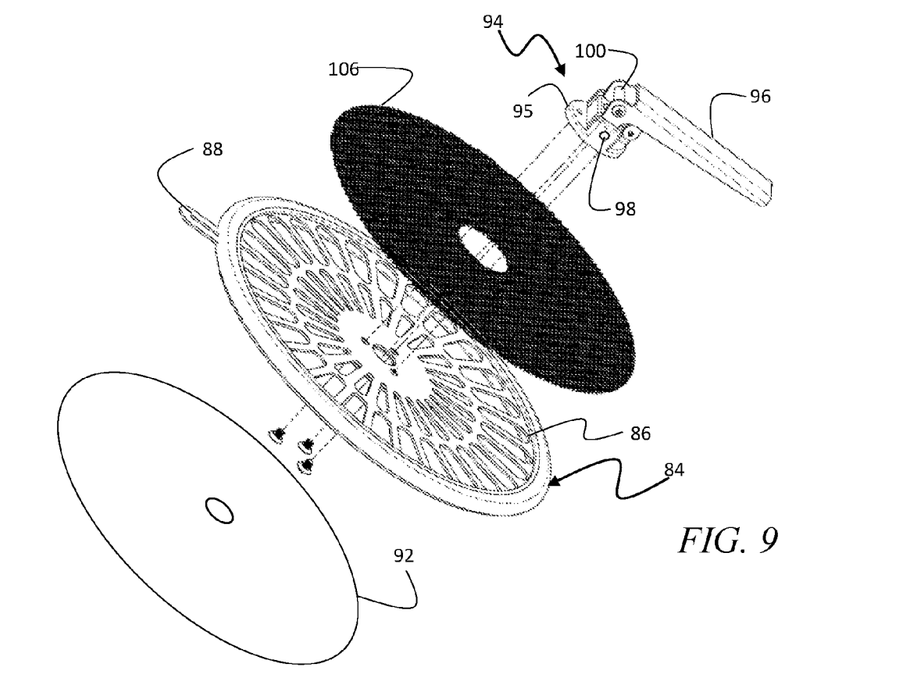
FIG. 9 is a perspective exploded view of the cover plate.

An exploded view of cover plate 84 is provided in FIG. 9. Cover plate 84 has a diameter larger than diameter of vent 76 and is configured to occlude apertures 78. Cover plate 84 contains a plurality of apertures 86 corresponding to apertures 78 of vent 76. Cover plate 84 contains a slot 88 configured to receive a tab 90 disposed on lateral wall 14 near vent 76. When tab 90 is within slot 88, apertures 86 of cover plate 84 align with apertures 78 of vent 76, thereby enabling sterilization agent flow therethrough. A vent filter 92 is sandwiched between exterior surface of vent 76 and inner surface of cover plate 84.

Figure 10:
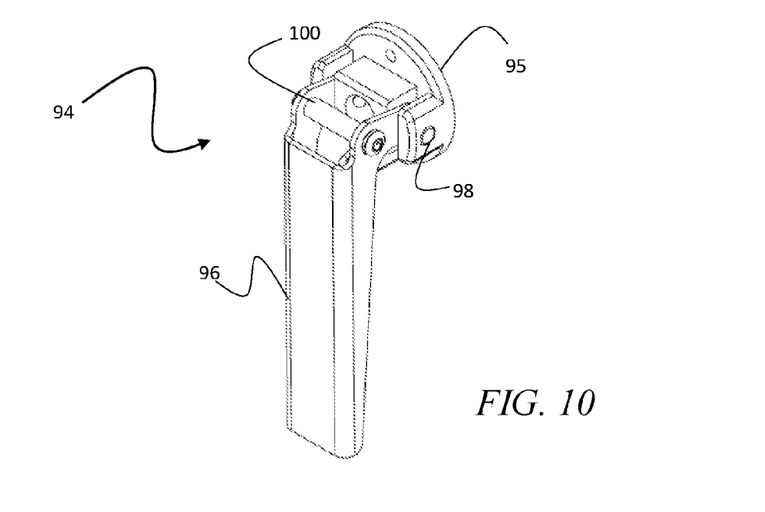
FIG. 10 is a perspective view of the latch disposed on the cover plate.

Cover plate 84 contains a latch 94 attached thereto. Latch 94 is depicted in FIG. 10. Latch 94 includes a latch handle 96 that is pivotally attached to latch base 95 via pivot 98. Latch handle 96 includes a locking pin 100. Latch 94 is configured to receive rod 80 through opening 102 when cover plate 84 is positioned over vent 76. As latch handle 96 is pivoted toward its locked downward facing configuration, a force must be applied onto cover plate 84 pressing it into lateral wall 14 of sterilization cabinet 10. In its locked configuration, locking pin 100 is received into notch 82 of rod 80. When locking pin 100 resides within notch 82, latch base 95 exerts a force onto cover plate 84 pressing cover plate 84 against lateral wall 14. A gasket 104 encircles periphery of cover plate 84. A second gasket 105 may be disposed around the inner circumference. The force exerted by latch base 95 onto cover plate 84 causes gaskets 104 and 105 to press against exterior surface of lateral wall 14. Gaskets 104 and 105 undergoes elastic deformation thereby creating a fluid-impermeable seal between cover plate 84 and exterior wall 14. The fluid-impermeable seal cannot be penetrated by gases, liquids, microbes, or other contaminants, thereby isolating the interior space of the sterilization cabinet from the environment. In an embodiment, cover plate 84 further includes a wire mesh 106 configured to protect vent filter 92 from getting punctured or damaged.

To replace vent filter 92, cover plate 84 is removed from vent 76. Latch handle 96 is pivoted upwards until locking pin 100 is released from notch 82 of rod 80. Once locking pin 100 is released, cover plate 84 and vent filter 92 may be removed. A new vent filter 92 may then be positioned over vent 76 and secured in that position by cover plate 84.

In alternative embodiments, different locking mechanisms for securing cover plate 84 over vent 76 may be used without departing from the scope of the invention. For example, cover plate 84 can be fastened to lateral wall 14 or otherwise attached thereto by any means so long as cover plate 84 forms a fluid-impermeable seal with exterior surface of lateral wall 14. The fluid-impermeable seal cannot be penetrated by gases, liquids, microbes, or other contaminants, thereby isolating the interior space of the sterilization cabinet from the environment. This configuration ensures that all sterilization agent flow must pass through vent filter 92. In an alternative embodiment, cover plate 84 may be disposed on the interior of sterilization cabinet 10. Cover plate 84 has a circular shape because this shape allows the forces exerted onto the center of cover plate 84 to be evenly distributed to the periphery of cover plate 84, thereby increasing the integrity of the fluid-impermeable seal. In alternative embodiments, cover plate 84 may have different shapes besides a circular shape depicted in the figures. Cover plate 84 may also have differently shaped apertures 86 that may be arranged in various configurations.

Figure 11:
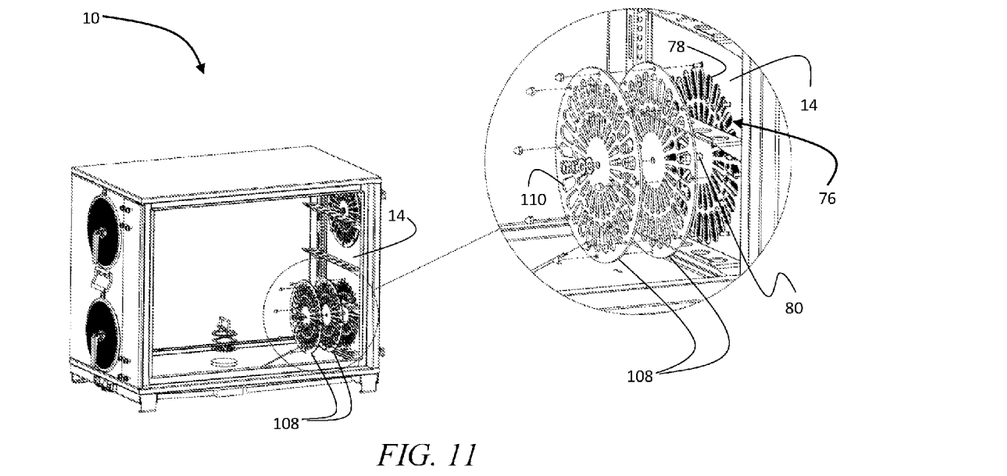
FIG. 11 is an enlarged exploded view depicting the reinforcement plates within the body of the sterilization cabinet.

Referring to FIG. 11, one or more reinforcement plates 108 may be disposed on the interior and/or exterior surface of lateral wall 14 over vent 76. Reinforcement plate 108 may contains a plurality of apertures 110 corresponding to apertures 78 of vent 76 and/or apertures 86 of cover plate 84. This structural configuration ensures that reinforcement plate 108 does not interfere with sterilization agent flow through vent 76. Distal end of rod 80 passes through a corresponding opening within reinforcement plate 108 and may be secured therein using nuts and washers. Reinforcement plate 108 provides added strength to lateral wall 14, thereby ensuring that lateral wall 14 does not deform when subjected to high temperatures and pressures. This ensures integrity of the microbe and fluid-impermeable seal formed between exterior surface of lateral wall 14 and cover plate 84 during and after a sterilization cycle. Multiple reinforcement plates 108 may be used to further strengthen lateral wall 14.

Figure 2:
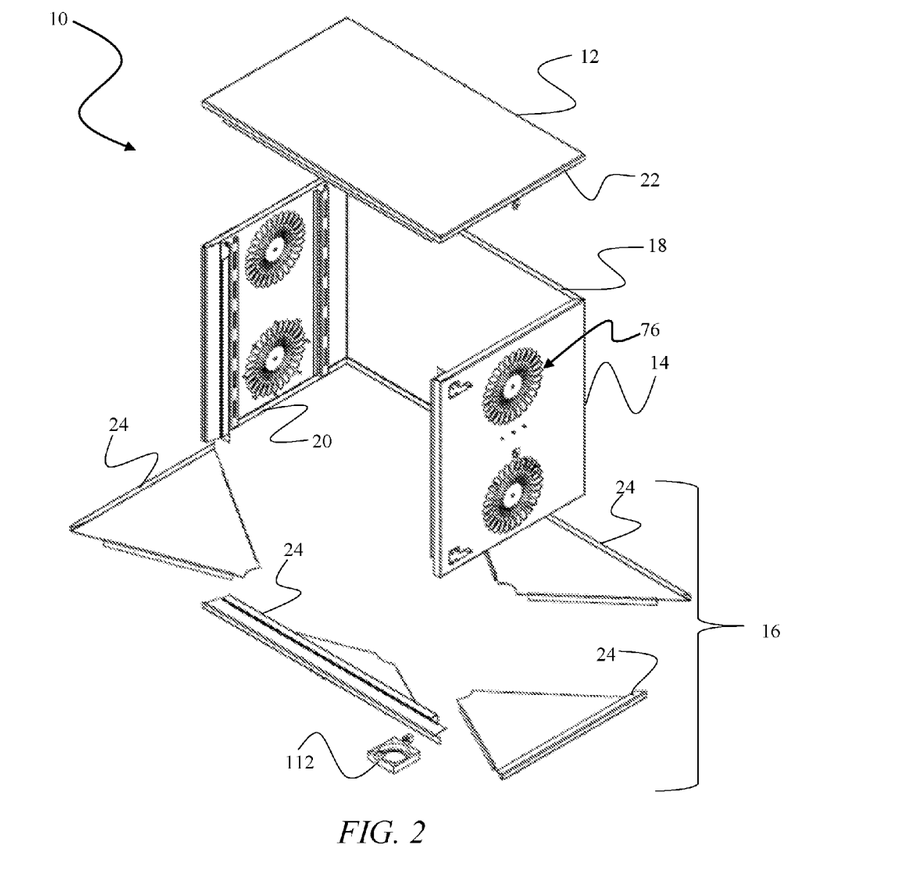
FIG. 2 is an exploded perspective view of the sterilization cabinet.
Figure 3:
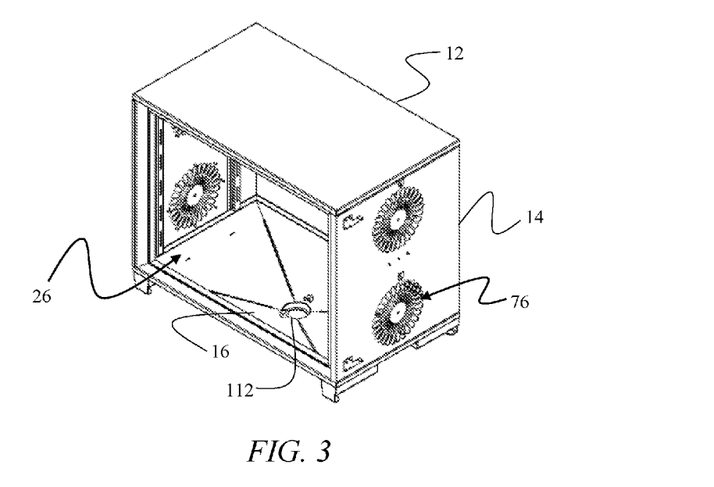
FIG. 3 is a perspective view of the body of the sterilization cabinet.

As illustrated in FIG. 2, two pairs of vent ports 76 may be positioned on opposite sides of lateral wall 14. Other configurations of vent ports 76 also fall within the scope of the invention. The total area of apertures 78 must be sufficiently large to permit adequate flow of sterilization agent required to sterilize the contents of sterilization cabinet 10 in a predetermined period of time. It is also important that dimensions and arrangement of apertures 78 do not compromise structural integrity of lateral wall 14. In some embodiments, vent ports 76 may be positioned on the back portion of later wall 14 and/or door 28.

Referring to FIGS. 2 and 3, sterilization cabinet 10 has a sloping floor 16. In the embodiment depicted in FIG. 2, floor 16 is made up of four panels, wherein each panel has flanges extending from its edges. The flanges are used to weld or fasten the four panel of floor 16 to one another and also to attach floor 16 to the bottom edges of lateral wall 14. Each section of floor 16 slopes downward from the periphery of sterilization cabinet 10 to its center. This structural configuration utilizes gravity to channel liquid contained within sterilization cabinet 10 toward the lowest point of floor 16. A drain assembly 110 is disposed at the lowest point of floor 16 enabling liquid to flow out of sterilization cabinet 10. In alternative embodiment, floor 16 may comprise any number of panels including a single sloping panel. Floor 16 may have channels, and may have any shape and configuration so long as it is configured to cause a liquid contained within sterilization cabinet 10 to flow into drain assembly 110.

Figure 12:
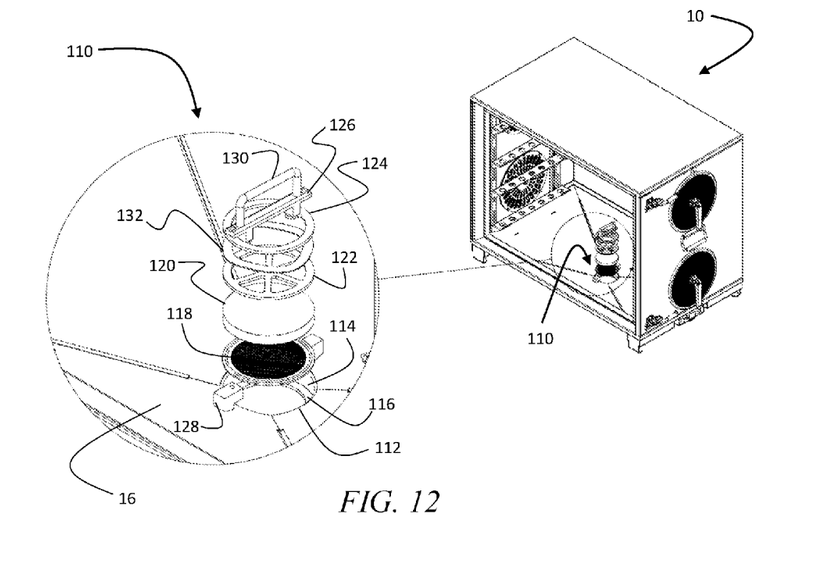
FIG. 12 is an enlarged exploded view of the drain assembly.

FIG. 12 depicts an exploded view of drain assembly 110. Drain assembly 110 comprises a drain port 112 disposed at the lowest point of floor 16. A drain wall 114 is affixed beneath drain port 12. Drain wall 114 has a flange 116 at the bottom thereof. A wire gasket 118 is placed in drain assembly 110 and rests on flange 116. One or more drain filters 120 are placed on top of wire gasket 118. One or more drain filters 120 permit liquids and gas to pass therethrough while preventing microbes and contaminants from entering the interior space of sterilization cabinet 10.

A filter support 122 is placed over drain filters 120. Filter support 122 is an annular disc within a plurality of spokes disposed therein providing structural support to drain filters 120. Thus, drain filters 120 are sandwiched between wire gasket 118 and filter support 122, whereby wire gasket 118 and filter support 122 provide adequate support to drain filters 120 to protect them from being damaged by high pressure and fluid flow to which they are subjected during the sterilization cycle.

Wire gasket 118, drain filters 120, and filter support 122 are retained within drain wall 114 by drain gate 124. Drain gate 124 contains an annular disc configured to not obstruct fluid flow through drain assembly 110. Drain gate 124 includes radially protruding tabs 126 configured to engage brackets 128 disposed on floor 16 near drain port 112. Drain gate 124 may include a handle 130 to enable the operator of sterilization cabinet 10 to close and open drain gate 124 by rotating it between a locked configuration in which tabs 126 engage brackets 128 and unlocked configuration in which tabs 126 disengage brackets 128.

A disk spring 132 may be disposed within drain wall 114 between filter support 122 and drain gate 124. Disk spring 132 accomplishes two objectives: first, it urges tabs 126 of drain gate 124 into brackets 128 thereby retaining drain gate 124 in its locked configuration. Tabs 126 may further contain indentations or holes configured to receive knobs positioned on brackets 128. To unlock drain gate 124, one must apply a downward force onto handle 130 sufficient to overcome the biasing force of disk spring 132 and then rotate handle 130 until tabs 126 disengage brackets 128. The second purpose of disk spring 132 is to press filter support 122 into wire gasket 118 thereby creating an air-tight, fluid-impermeable seal therebetween. This configuration constrains fluid flow to pass through drain filters 120. Wire gasket 118 may have a seal disposed around its periphery. Other means of sealingly securing drain filter 120 within drain assembly 110 are also within the scope of the invention.

To use the invention disclosed herein, an operator places objects to be sterilized into sterilization cabinet 10 through access port 26 and closes door 28. When door 28 is in its closed configuration, the interior space of sterilization cabinet 10 is sealed from the external environment. The only inlets and outlets of sterilization agent flow between the interior and exterior of sterilization cabinet 10 occur through vent filters 92 disposed within vent ports 76 and drain filter 120 disposed within drain assembly 110. This configuration ensures that sterilization agent is able enter and exit sterilization cabinet 10 through vent ports 76 and drain assembly 110 during sterilization cycle while ensuring that the interior space of sterilization cabinet 10 remains isolated from the ambient environment after the sterilization cycle has been completed. Any condensate produces within sterilization cabinet 10 is channeled by gravity along sloping floor 16 into drain assembly 110, through which condensate is expelled from sterilization cabinet 10, during the drying phase of the sterilization cycle, thereby ensuring that no excess moisture remains within sterilization cabinet 10.

In an alternative embodiment, drain assembly 110 may contain a valve configured to permit condensate to exit sterilization cabinet 10 while preventing ambient air from entering sterilization cabinet 10. The valve may be configured to open and close responsive to the pressure level inside sterilization cabinet 10. For example, when the pressure inside cabinet 10 is greater than the ambient pressure, the valve may be opened to expel liquid condensate created during sterilization cycle. When the difference between the interior and ambient pressures falls below a predefined threshold, the valve may be configured to close to prevent microbes and contaminants from entering the cabinet. In alternative, the valve may be configured to open and close responsive to a predetermined temperature or at a predetermined time.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

GLOSSARY OF THE CLAIM TERMS

Access port—an opening within the body of the sterilization cabinet through which the interior space of the sterilization cabinet can be accessed to load and unload medical instruments or other objects.

Body—a casing enclosing an interior space of the sterilization cabinet.

Cover plate—a component that attaches to the body of the cabinet over the vent port and is configured to retain a filter.

Drain assembly—a component of the sterilization cabinet that expels the liquid condensate from the interior space of the sterilization cabinet.

Drain port—an opening dispose within the body of the sterilization cabinet through which liquid condensate exits the interior space of the cabinet.

Filter—an object permitting steam and air to pass therethrough, while preventing passage of microbes and contaminants.

Floor—a bottom panel of the body of the sterilization cabinet.

Fluid-impermeable seal—a connection between two components that cannot be penetrated by gas, liquid, microbes, or contaminates capable of compromising sterility of the objects contained within the sterilization cabinet.

Hinge arm—a component of the hinge assembly that is stationarily affixed to the body of the sterilization cabinet and is pivotally connected to the hinge link.

Hinge assembly—an apparatus hingedly connecting the door to the body of the sterilization cabinet.

Hinge base—a component of the hinge assembly affixed to the body of the sterilization cabinet configured to retain the hinge shaft.

Hinge shaft—an elongated component at least one end of which resides within the hinge base. Hinge shaft connects the hinge arm to the hinge base.

Latch—an apparatus used to selectively secure the cover plate over the vent port. The latch may have a movable handle used to transition the latch between its locked and unlocked configurations.

Lateral wall—a portion of the body of the sterilization cabinet disposed between the roof and floor. The lateral wall may comprise a plurality of panels: for example, a right panel, a left panel, and a back panel. The lateral wall may also be a single panel. The lateral wall may have a sectional shape, a curved shape, or a combination thereof. Other configurations are also within the scope of the invention.

Reinforcement plate—a component that is disposed over the vent port used to fortify the body of the sterilization cabinet.

Roof—a top panel of the body of the sterilization cabinet.

Sterilization agent—a substance that is used to sterilize objects contained within sterilization cabinet. Sterilization agent may be steam, hot air, a chemical, or any other substance capable of killing microbes and other living organisms.

Vent port—an aperture or a plurality of apertures disposed within the body of the sterilization cabinet through which sterilization agent can enter and/or exit the sterilization cabinet.

What is claimed is:
1. A sterilization cabinet, comprising:
a roof, a lateral wall, and a floor collectively forming a body of the sterilization cabinet partially enclosing an interior space, wherein the interior space of the sterilization cabinet is accessible through an access port defined by proximal edges of the roof, the lateral wall, and the floor;
a door transitional between an open configuration and a closed configuration, wherein in the closed configuration, the door encloses the interior space of the sterilization cabinet by occluding the access port and forming a first fluid-impermeable seal therewith;
a plurality of vent apertures disposed within the lateral wall or the door of the sterilization cabinet;
a first filter occluding the plurality of vent apertures, whereby a fluid must pass through the first filter to enter or exit the interior space of the sterilization cabinet through the plurality of vent apertures;
a drain assembly having a drain port disposed within the floor, wherein the floor has a slope configured to cause a liquid contained within the interior space of the sterilization cabinet to flow into the drain port, wherein the liquid within the interior space of the sterilization cabinet exits therefrom only through the drain port; and
a second filter sealingly enclosed within the drain assembly, wherein the liquid is constrained to pass through the second filter to enter or exit the interior space of the sterilization cabinet through the drain port;
whereby when the door is in the closed configuration, all sterilization agent flow between interior space of the sterilization cabinet and an external environment must pass through the first filter, the second filter, or both.

2. The sterilization cabinet according to claim 1, wherein at least one of the plurality of vent apertures is tear-shaped, circular, oval, elliptical, or a combination thereof.

3. The sterilization cabinet according to claim 1, further comprising a cover plate retaining the first filter over the plurality of vent apertures.

4. The sterilization cabinet according to claim 3, further comprising a latch, wherein the latch exerts a force onto the cover plate thereby retaining the first filter in a sandwiched relation between the cover plate and the plurality of vent apertures.

5. The sterilization cabinet according to claim 4, further comprising a gasket disposed on the cover plate, wherein the force applied onto the cover plate by the latch causes the gasket to undergo an elastic deformation thereby creating the second fluid-impermeable seal with the body or the door of the sterilization cabinet.

6. The sterilization cabinet according to claim 4, further comprising a rod extending from the body of the sterilization cabinet, the rod having a notch, wherein the latch is configured to retain the cover plate by accepting the rod and engaging the notch thereon.

7. The sterilization cabinet according to claim 3, further comprising a wire mesh disposed on the cover plate.

8. The sterilization cabinet according to claim 1, further comprising a reinforcement plate disposed within the body of the sterilization cabinet, wherein the reinforcement plate has an opening at least partially coinciding with at least one of the plurality of vent apertures thereby permitting sterilization agent to flow therethrough.

9. The sterilization cabinet according to claim 1, wherein the door is connected to the body of the sterilization cabinet by a hinge assembly.

10. The sterilization cabinet according to claim 9, the hinge assembly comprising:
a hinge base affixed to the body of the sterilization cabinet, the hinge base configured to accept a hinge shaft;
a first hinge arm accepting the hinge shaft, the first hinge arm having a first gear;
a second gear affixed to the door;
a hinge link pivotally connected to the first gear and the second gear, whereby the door can rotate with respect to the body of the sterilization cabinet by at least 270 degrees.

11. The sterilization cabinet according to claim 10, wherein an angle of inclination, a horizontal position, and a vertical position of the door with respect to the access port of the sterilization cabinet can be adjusted by adjusting positions or angles of the hinge base, the hinge shaft, and the first hinge arm.

12. A sterilization cabinet, comprising:
a body partially enclosing an interior space, wherein the interior space of the sterilization cabinet is accessible through an access port defined by a roof, a floor, and a lateral wall collectively forming the body;
a door in mechanical communication with the body of the sterilization cabinet, the door transitional between an open configuration and a closed configuration, wherein in the closed configuration, the door encloses the interior space of the sterilization cabinet by occluding the access port and forming a first fluid-impermeable seal therewith;
a plurality of apertures disposed within the lateral wall or the door of the sterilization cabinet, the plurality of apertures collectively forming a first vent port;
a first filter occluding the plurality of apertures wherein a fluid must pass through the first filter to enter the interior space of the sterilization cabinet, thereby the first filter maintaining sterility of objects contained within the sterilization cabinet;
a drain assembly having a drain port disposed at a lowest point of the body of the sterilization cabinet, wherein a shape of the floor is configured to cause a liquid contained within the interior space of the sterilization cabinet to flow into the drain port, whereby the liquid within the interior space of the sterilization cabinet drains therefrom only through the drain port;
wherein the drain assembly is configured to expel liquid from the sterilization cabinet and to preclude contaminants from entering the interior space of the sterilization cabinet through the drain port.

13. The sterilization cabinet according to claim 12, further comprising a cover plate configured to retain the first filter in a sandwiched relation to the first vent port.

14. The sterilization cabinet according to claim 13, wherein the force applied onto the cover plate is exerted by a locking mechanism, the locking mechanism accepting a rod extending from the body of the sterilization cabinet and engaging a notch disposed on the rod.

15. The sterilization cabinet according to claim 14, further comprising a gasket disposed on the cover plate, wherein the force applied onto the cover plate causes the gasket to undergo an elastic deformation thereby creating the second fluid-impermeable seal between the cover plate and the body of the sterilization cabinet.

16. The sterilization cabinet according to claim 12, further comprising a reinforcement plate disposed within the body of the sterilization cabinet, wherein the reinforcement plate has an opening at least partially coinciding with at least one of the plurality of the vent apertures thereby permitting sterilization agent to flow therethrough.

17. The sterilization cabinet according to claim 12, wherein the door is connected to the body of the sterilization cabinet by a hinge assembly.

18. The sterilization cabinet according to claim 17, wherein an angle of inclination, a horizontal position, and a vertical position of the door with respect to the access port of the sterilization cabinet can be adjusted by adjusting positions or angles of the hinge base, the hinge shaft, and the first hinge arm.

19. The sterilization cabinet according to claim 17, wherein the hinge assembly enables the door to rotate with respect to the body of the sterilization cabinet by at least 270 degrees.

20. The sterilization cabinet according to claim 17, further comprising a damper configured to allow the door to stop at any angle of rotation.

* * * * *